US00PP34625P2

(12) United States Plant Patent
Sidhu

(10) Patent No.: US PP34,625 P2
(45) Date of Patent: Oct. 4, 2022

(54) ***GAULTHERIA* PLANT NAMED 'GAULSIDH12'**

(50) Latin Name: *Gaultheria shallon*
Varietal Denomination: Gaulsidh12

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 0 days.

(21) Appl. No.: 17/701,052

(22) Filed: Mar. 22, 2022

(30) Foreign Application Priority Data

Apr. 15, 2021 (CA) ..... CA 2110463

(51) Int. Cl.
*A01H 6/36* (2018.01)
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Gaultheria shallon* plant named 'Gaulsidh12' that is characterized by its new foliage and stem growth that is red in color, its leaves that are narrow and pointed, and its broadly spreading plant habit.

2 Drawing Sheets

Botanical classification: *Gaultheria shallon.*
Cultivar designation: 'Gaulsidh12'.

CROSS REFERENCE TO RELATED APPLICATIONS

This application claims priority to a Canadian Plant Breeder's Rights Application No. 21-10463 filed on Apr. 15, 2021, under 35 U.S.C. 119(f), the entire contents of which is incorporated by reference herein. This application is also co-pending with a U.S. Plant Patent Application filed for a plant derived from the same breeding program that is entitled *Gaultheria* Plant Named 'Gaulsidh4' (U.S. Plant patent application Ser. No. 17/701,023).

BACKGROUND OF THE INVENTION

The present invention relates to a new and distinct cultivar of *Gaultheria shallon*, botanically known as *Gaultheria shallon* 'Gaulsidh12' and is hereinafter referred to by its cultivar name 'Gaulsidh12'.

'Gaulsidh12' was discovered by the Inventor as a chance seedling that was growing in a container in Mission, B.C., Canada in spring of 2017. The containers had been planted with seed derived from unnamed and unpatented plants of *Gaultheria shallon*. The exact parents are unknown.

Asexual propagation of the new cultivar was first accomplished by tissue culture using meristemac tissue under the direction of the Inventor in Mission, B.C., Canada in spring of 2018. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Gaulsidh12' as a new and unique cultivar of *Gaultheria.*

1. 'Gaulsidh12' exhibits new foliage and stem growth that is red in color.
2. 'Gaulsidh12' exhibits leaves that are narrow and pointed.
3. 'Gaulsidh12' exhibits a broadly spreading plant habit.

'Gaulsidh12' can be most closely compared to typical plants of *Gaultheria shallon* and 'Gaulsidh4'. Both are similar to 'Gaulsidh12' in flower color. Typical plants of *Gaultheria shallon* differ from 'Gaulsidh12' in having leaves that are ovate to almost round in shape and in having new growth that is green in color. 'Gaulsidh4' differs from 'Gaulsidh12' in having a very compact plant habit, a smaller plant size, leaves that are smaller in size and more rounded in shape, new growth that is green in color, and in producing more flowers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Sidhu & Sons Nursery, Nursery Guide, British Columbia landscape and Nursery Association, Bremerton City Nursery, Shoot Gardening, Green Flow Nurseries, Plant Something B.C., Gardenzia, Farwest Show, Briggs Nursery, and Herman Losely & Son.

BRIEF DESCRIPTION OF THE DRAWINGS

The accompanying color photographs illustrate the overall appearance and distinct characteristics of two year-old plants as grown outdoors in 1-gallon containers in St. Thomas, Ontario, Canada.

The photograph in FIG. 1 provides a side view of 'Gaulsidh12' in fruit.

Figure 1:
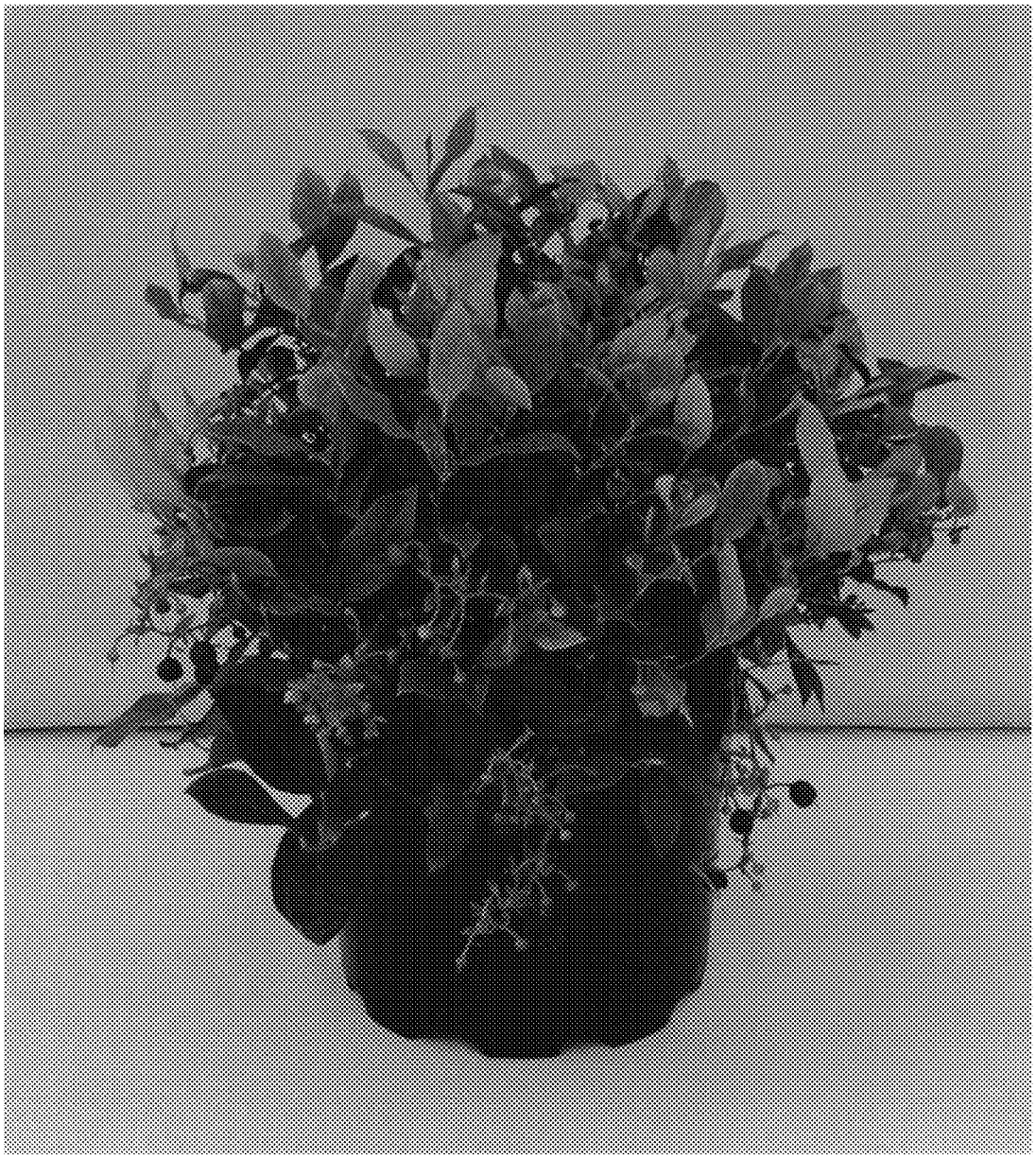
Figure 2:
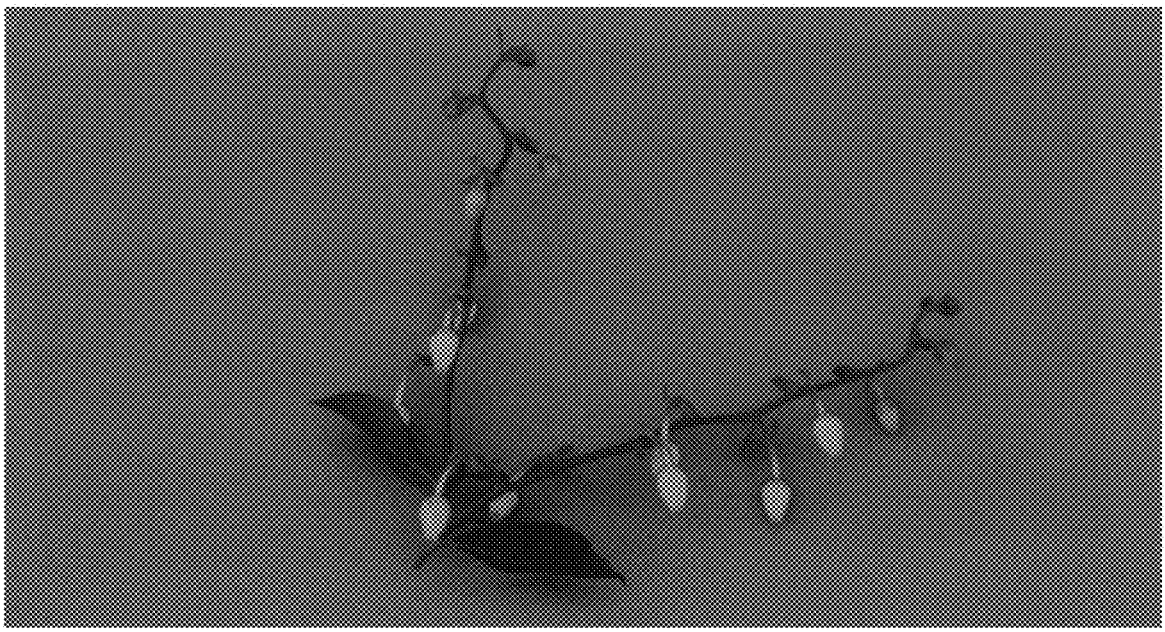

The photograph in FIG. 2 provides a close-up view of the flowers of 'Gaulsidh12'.

Figure 3:
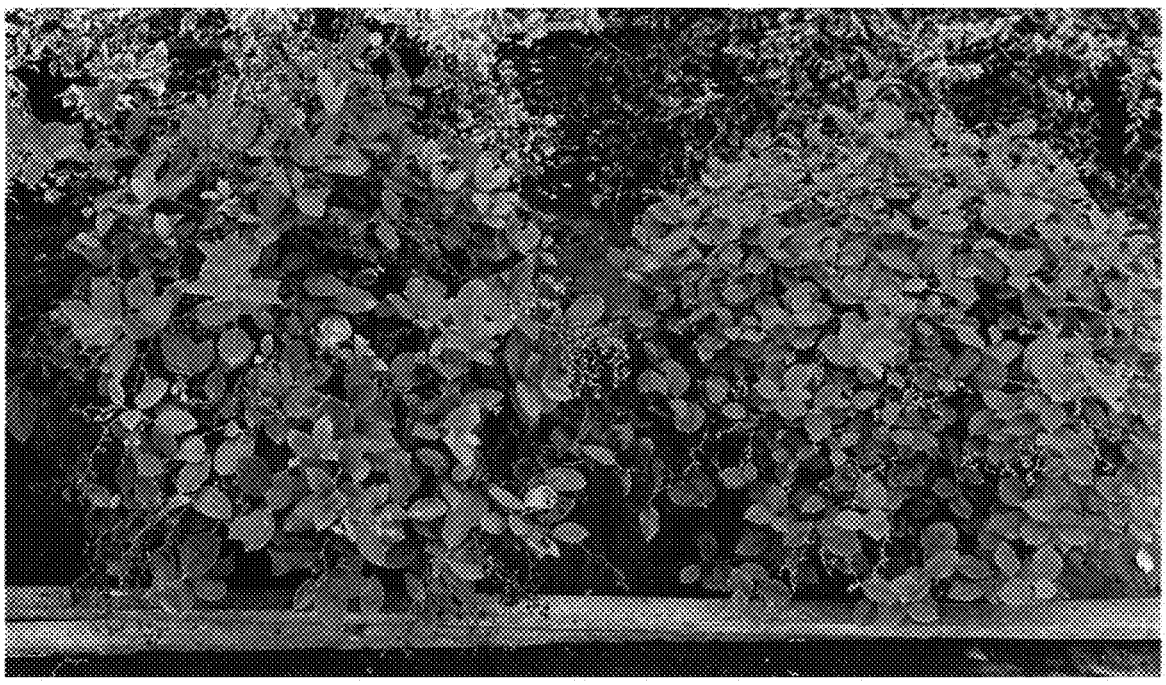

The photograph in FIG. 3 provides a comparison view between 'Gaulsidh12' (left) and 'Gaulsidh4' (right).

The colors in the photographs may differ slightly from the color values cited in the detailed botanical description, which accurately describe the colors of the new *Gaultheria*.

DETAILED BOTANICAL DESCRIPTION OF THE PLANT

The following is a detailed description of 2.5-year-old plants of the new cultivar grown outdoors in 1-gallon containers in St. Thomas, Ontario, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Four to six weeks from late spring to late summer in Ontario, Canada.

*Plant type.*—Evergreen shrub.

*Plant habit.*—Broadly spreading.

*Plant shape.*—Oblate.

*Height and spread.*—Reaching an average of 30 cm in height and 50 cm in width as a 2.5 year-old plant in a one-gallon container, and 60 cm in height by 90 cm in width in the landscape.

*Cold hardiness.*—At least in U.S.D.A. Zone 6.

*Diseases and Pests.*—No resistance or susceptibility to diseases or pests has been observed.

*Propagation.*—Tissue culture.

*Root development.*—6 weeks to initiate roots in tissue culture, an average of 12 months to produce a 1-gallon plant.

*Growth rate and vigor.*—Moderate.

Stem description:

*Shape.*—Round.

*Stem color.*—New stem; 181B, non-sunny side 144C, mature; 144C to 144D.

*Stem size.*—An average of 23 cm in length and 2.7 mm in width.

*Stem surface.*—Smooth and pubescent.

*Stem strength.*—Medium to strong.

*Branching.*—Freely branched, an average of 24 basal branches each with approximately 10 secondary branches.

*Branch angle.*—Upright to outward.

*Branch internode length.*—Up to 2.3 cm.

Foliage description:

*Leaf shape.*—Young leaves; elliptic to obovate, mature leaves; elliptic.

*Leaf division.*—Simple.

*Leaf base.*—Cuneate, wedged.

*Leaf apex.*—Acute to cuspidate.

*Leaf fragrance.*—Wintergreen if crushed.

*Leaf venation.*—Pinnate, young leaf color; mid vein of upper surface 144A, mid vein of lower surface 145A, mature leaf color; mid vein of upper surface 145B, mid vein of lower surface; close to 146C.

*Leaf margins.*—Irregularly serrate, single small hair emerging from the tip of each tooth, up to 1 mm in length and 166B in color.

*Leaf arrangement.*—Alternate and clustered near tips.

*Leaf attachment.*—Petiolate.

*Leaf number.*—Average of 9 per branch.

*Leaf surface.*—Upper and lower surface; smooth, glabrous, moderately glossy and leathery.

*Leaf variegation.*—Absent.

*Leaf size.*—Average of 6 cm in length and 3.4 cm in width.

*Leaf color.*—Emerging leaves upper surface; 166C and 144D, margins 184A, emerging leaves lower surface, 174B and 144C, margins 181C, young leaves upper surface; 144A, young leaves lower surface; 146D, mature leaves upper surface; 147A, mature leaves lower surface; 147B.

*Petioles.*—Average of 5.4 mm in length and 1.8 mm in width, upper and lower surfaces are dull, color of upper and lower surfaces; 145C.

Inflorescence description:

*Inflorescence.*—Axillary and terminal clusters of individual flowers.

*Inflorescence size.*—Average of 13 cm in length.

*Lastingness of inflorescence.*—Average of 2 weeks, self cleaning (sepals and petals).

*Number of flowers.*—4 to 10 per flowering branch, average of 150 per plant.

*Flower buds.*—Ovate in shape, average of 4 mm in length and 3 mm in width, color NN155B suffused with 63C towards base, satiny surface.

*Flower size.*—Average of 9 mm in length and 7 mm in width.

*Corolla.*—Urceolate in shape, comprised of 5 fused ovate shaped petals with rounded tips (5%) free that are moderately reflexed, free parts are 1.5 mm in length and 1 mm width, width of aperature 4 mm, color NN155B on both surfaces, when opening and mature, both surfaces are satiny and glabrous and very slightly ribbed on inner and outer surfaces.

*Calyx.*—Rotate in arrangement, average of 5 mm in depth and 7 mm in diameter.

*Sepals.*—5, ovate in shape with base fused (lower 25% fused into ring), average of about 4 mm in length and 3 mm in width, acute apex, color 155B suffused with 62B towards base, dull on both surfaces, moderately pubescent about lmm in length and 185A in color.

*Bracts.*—2 small bracts, an average of 1 mm in length and width, ovate in shape, truncate base, acute apex, glossy on both surfaces, color 155B suffused with 62B.

*Peduncles.*—Round, curved to hang downward, an average of 2 mm in length and 1 mm in width, 185B in color, pubescent surface.

*Pedicels.*—None, peduncles arise directly from stem node.

Reproductive organs:

*Androecium.*—Stamens; average of 10, anthers; dorsifixed, narrow deltoid in shape, 60B in color and 2 mm in length, filaments; oblong in shape, 4 mm in length, 1 mm in width and 145D in color, highly pubescent, pollen; moderate in quantity and NN155C in color.

*Gynoecium.*—Pistil; 1, stigma; club-shaped, 1 mm in length and width, 145D in color, style; average of 6 mm in length, 157D in color, ovary; round in shape, 6-parted, 2.5 mm in diameter and depth, 145C in color.

Fruit description:

*Type.*—Berry.

*Number.*—Average of 5 to 8 per lateral branch.

*Fruit size.*—Up to 1.2 cm in length and width.

*Fruit skin color.*—Young fruit; 183A, mature fruit; 202A.

*Fruit flesh.*—155B in color, glistening and spongy in texture.

*Fruit surface.*—Slightly glossy and glabrous.

*Fruit shape.*—Oblate with indented apex and 5 bluntly acute extended tips, tip size is 5 mm in length and 6 mm in width, persistent style, 3 mm in length.

*Seeds.*—Approximately 28 cylindrical shaped seeds, glossy surface, less than 1 mm in length and width, 160D in color.

It is claimed:

1. A new and distinct cultivar of *Gaultheria* plant named 'Gaulsidh12' as herein illustrated and described.

* * * * *